United States Patent [19]
Grosslight

[11] Patent Number: 5,847,330
[45] Date of Patent: Dec. 8, 1998

[54] STETHOSCOPE WITH REMOVABLE HANDLES FOR SINGLE-HANDED OPERATION

[75] Inventor: James Theodore Grosslight, Apex, N.C.

[73] Assignee: Adstracts Inc., Raleigh, N.C.

[21] Appl. No.: 82,199

[22] Filed: May 20, 1998

[51] Int. Cl.$^6$ .................................................... A61B 7/02
[52] U.S. Cl. ........................................................ 181/131
[58] Field of Search ................................. 181/131, 137, 181/141; 381/67

[56] References Cited

U.S. PATENT DOCUMENTS

| | | | |
|---|---|---|---|
| 4,011,925 | 3/1977 | French et al. ......................... | 181/131 |
| 4,149,610 | 4/1979 | Saiya et al. ........................... | 181/131 |
| 4,406,346 | 9/1983 | Pope, Jr. ............................... | 181/131 |
| 5,466,898 | 11/1995 | Gilbert et al. ........................ | 181/131 |

*Primary Examiner*—Khanh Dang
*Attorney, Agent, or Firm*—Myers Bigel Sibley & Sajovec

[57] ABSTRACT

A pair of handles removably secured to a stethoscope enable users to single-handedly mount and remove the headset to and from his or her head. By squeezing the handles together, a user can separate the upper ends of the rigid tubes of a stethoscope headset against the force of the biasing mechanism of the stethoscope. Each handle includes a channel configured to coaxially secure therewithin an ear tube and flexible tubing connected to the ear tube. A portion of the channel is configured to removably secure the ear tube and an adjacent portion is configured to removably secure a portion of the flexible tubing connected to the ear tube.

18 Claims, 2 Drawing Sheets

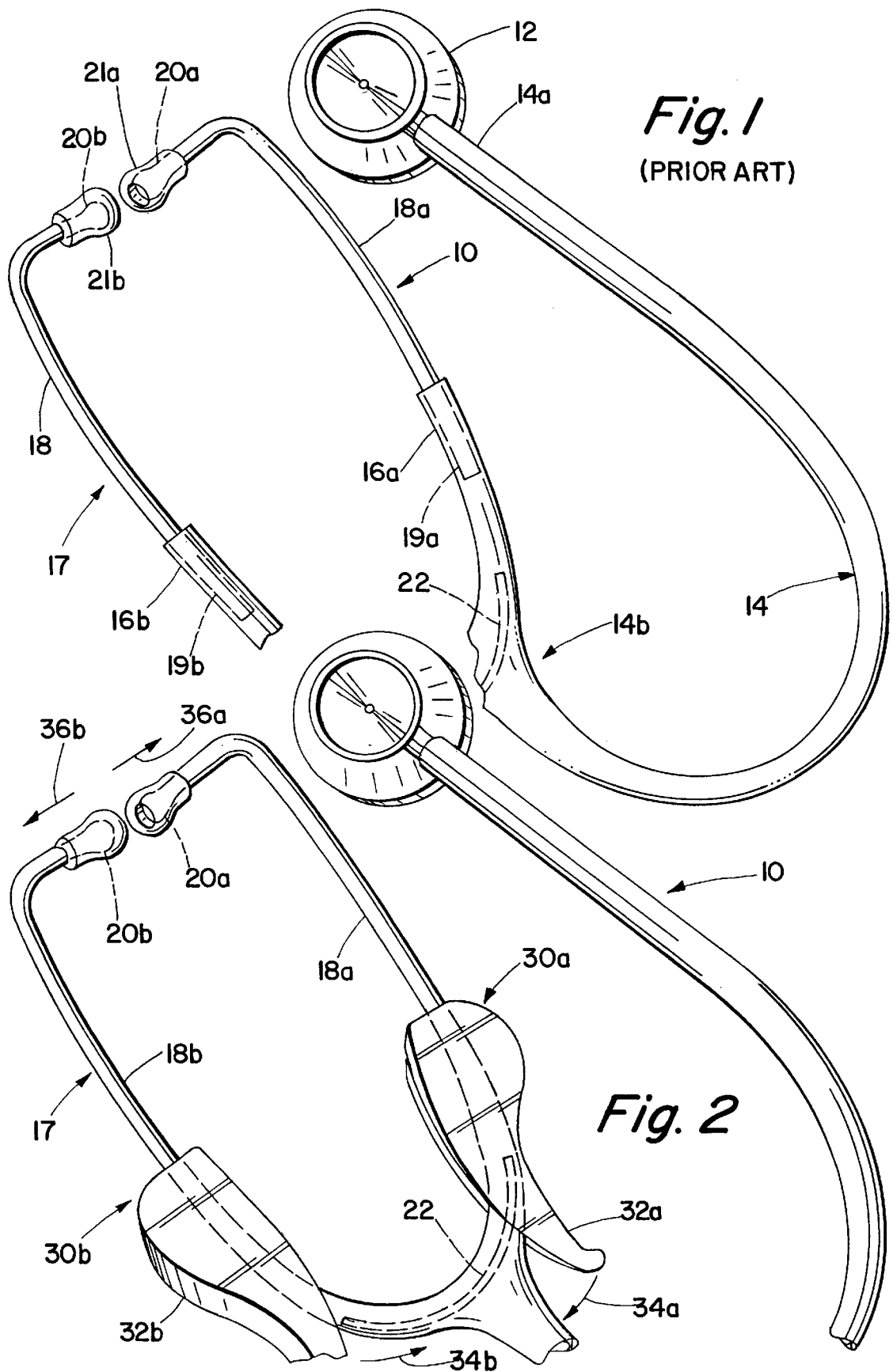

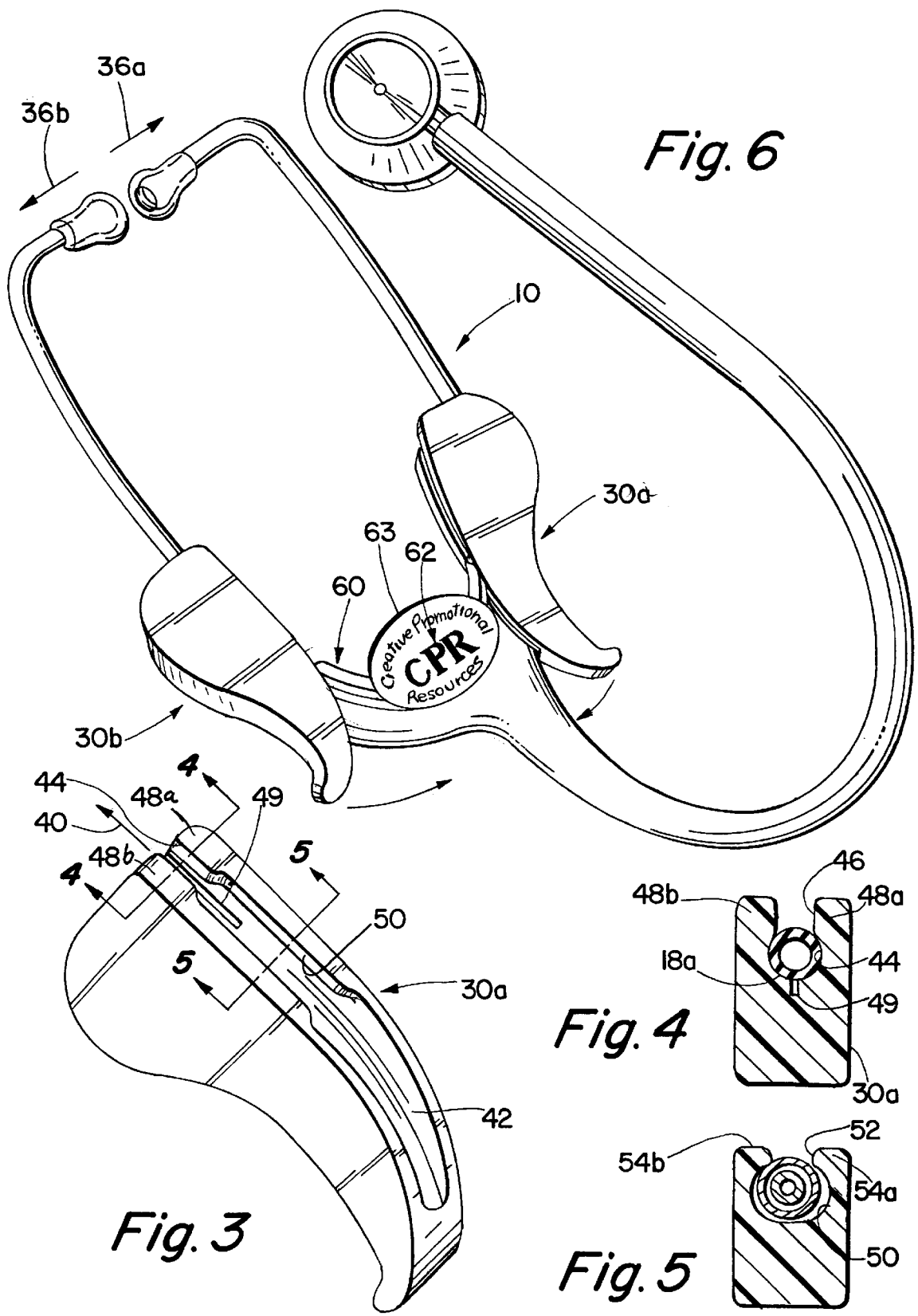

STETHOSCOPE WITH REMOVABLE HANDLES FOR SINGLE-HANDED OPERATION

FIELD OF THE INVENTION

The present invention relates generally to headsets and, more particularly, to stethoscope headsets.

BACKGROUND OF THE INVENTION

Stethoscopes conventionally include an acoustical transducer for detecting sounds from a patient's body. The acoustical transducer is conventionally connected to flexible tubing having a Y-shaped configuration. A substantially rigid tubular member having an ear piece conventionally extends from each branch of the Y-shaped flexible tubing and is intended to supply sound waves from the acoustical transducer to the ears of a user.

A conventional stethoscope 10 is illustrated in FIG. 1. An acoustical transducer 12 is connected to one end 14a of a flexible tube 14, as illustrated. The opposite end 14b of the flexible tube 14 has a Y-shaped configuration with branches 16a, 16b extending therefrom and is configured to acoustically attach to a headset 17. The headset 17 includes a pair of substantially rigid ear tubes 18a, 18b having lower ends 19a, 19b inserted within respective branches 16a, 16b of the flexible tube 14, as illustrated. The upper ends 20a, 20b of each of the rigid ear tubes 18a, 18b are fitted with ear pieces 21a, 21b for supplying sound from the rigid ear tubes 18a, 18b to the ears of a user. The rigid tubes 18a, 18b are biased towards one another via a spring 22 so that the headset 17 remains properly attached to the ears of a user. In the illustrated stethoscope 10 of FIG. 1, the spring 22 is connected to the lower ends 19a, 19b of the rigid ear tubes 18a, 18b and is enclosed within the Y-shaped portion of the flexible tubing 14.

A problem with the type of stethoscope 10 illustrated in FIG. 1 is that the headset 17 of the stethoscope 10 is conventionally mounted on the head of the user using two hands, one hand holding each of the two rigid ear tubes 18a, 18b. Similarly, the headset 17 is conventionally removed from the head of the user using two hands. Unfortunately, this is extremely inconvenient when a physician wishes to perform other functions for a patient with one of his or her hands.

U.S. Pat. No. 4,406,346 to Pope, Jr. describes a stethoscope having two tubular members extending from the ear pieces thereof that facilitate one-handed manipulation of the stethoscope headset. The extended members may be either integral with the tubes of the stethoscope or may be incorporated into the stethoscope as additional elements. Unfortunately, when the extended members are provided as an integral part of a stethoscope as described by Pope, Jr., manufacturing costs may be increased because of the somewhat complex configuration. When the extended members are provided as separate elements as described by Pope, Jr., a user is required to disassemble the stethoscope, couple the extended members to the tubes thereof, and then reassemble the stethoscope. Unfortunately, disassembly and reassembly of a stethoscope may be somewhat difficult and inconvenient to a user.

SUMMARY OF THE INVENTION

It is, therefore, an object of the present invention to provide a stethoscope having a headset that can be mounted and removed easily from the head of a user using only one hand.

It is another object of the present invention to provide an apparatus for allowing one-handed mounting and removal of stethoscope headsets that is inexpensive to manufacture.

It is another object of the present invention to provide an apparatus for allowing one-handed mounting and removal of stethoscope headsets that can be quickly and easily adapted to a stethoscope without requiring the stethoscope to be disassembled.

These and other objects of the present invention are provided by a pair of handles removably secured to a stethoscope for enabling a user to single-handedly mount and remove the headset of the stethoscope to and from his or her head. The handles are configured to allow a user to easily separate the upper ends of the rigid ear tubes of a stethoscope headset against the force of the biasing mechanism of the stethoscope. Each handle includes a channel configured to coaxially secure therewithin an ear tube and flexible tubing connected to the ear tube. A small diameter bore portion of the channel is configured to removably secure the ear tube and a large diameter bore portion is configured to removably secure a portion of the flexible tubing connected to the ear tube.

The handles according to the present invention can be inexpensive to manufacture. In addition, the handles may be quickly and easily installed and removed from a stethoscope without requiring disassembly of the stethoscope. Furthermore, the handles may be utilized with virtually any type of stethoscope.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 1 illustrates a conventional stethoscope as described above.

FIG. 2 illustrates handles adapted to the stethoscope of FIG. 1 for enabling single-handed operation of the headset of the stethoscope, according to an embodiment of the present invention.

FIG. 3 is a perspective view of a handle for enabling single-handed operation of a stethoscope headset, according to the present invention.

FIG. 4 is a sectional view of the handle of FIG. 3 taken along lines 4—4.

FIG. 5 is a sectional view of the handle of FIG. 3 taken along lines 5—5.

FIG. 6 illustrates handles adapted to the stethoscope of FIG. 1 for enabling single-handed operation of the ear pieces of the stethoscope, according to another embodiment of the present invention.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Referring now to FIG. 2, a pair of handles 30a, 30b having an elongated configuration are removably secured to the stethoscope 10 of FIG. 1 for enabling a user to single-handedly mount and remove the headset 17 from his or her head. The handles 30a, 30b are configured to allow a user to separate the upper ends 20a, 20b of the rigid ear tubes 18a, 18b against the force of the spring 22. As will be described in detail below, a portion of each handle 30a, 30b is configured to removably secure a respective ear tube 18a, 18b. In addition, a portion of each handle 30a, 30b is configured to removably secure a portion of the flexible tubing connected to each respective ear tube 18a, 18b.

The handles 30a, 30b may be formed from various materials including polymeric materials, wood and metals. Preferably, the handles 30a, 30b are formed from a moldable polymeric material using known techniques such as injection molding and extrusion. Accordingly, the handles 30a, 30b are relatively inexpensive to manufacture.

Still referring to FIG. 2, each of the handles 30a, 30b has an arcuate end portion 32a, 32b configured to be gripped by a hand of a user. As illustrated, the arcuate end portion 32a, 32b of each handle 30a, 30b extends in a direction away from the upper ends 20a, 20b of the rigid ear tubes 18a, 18b. This arcuate configuration helps provide leverage for separating the upper ends 20a, 20b of the rigid ear tubes 18a, 18b against the force of the spring 22. Arrows 34a, 34b indicate the direction that each arcuate end portion 32a, 32b moves when a user squeezes the pair of handles 30a, 30b. Arrows 36a, 36b indicate the corresponding direction that the upper ends 20a, 20b of the rigid ear tubes 18a, 18b move in response to a user squeezing the pair of handles 30a, 30b.

Referring now to FIG. 3, handles 30a, 30b will be described. Because each of the handles 30a, 30b are identical, only handle 30a will be described. The handle 30a defines a longitudinal direction, indicated by arrow 40. A channel 42 is formed in the handle 30a along the longitudinal direction 40, as illustrated. The channel 42 includes a small diameter bore portion 44 that is configured to secure the ear tube 18a coaxially positioned within the channel 42.

Referring now to FIG. 4, a sectional view of the small diameter bore portion 44 is illustrated. The ear tube 18a is shown coaxially positioned within the small diameter bore portion 44. The upper channel portion 46 of the small diameter bore portion 44 has a width less than the diameter of the small diameter bore portion 44. This upper portion 46 is formed by opposing walls 48a, 48b which have a generally arcuate configuration, as illustrated. A longitudinally extending slot 49 is formed in the handle opposite from the channel upper portion 46, as illustrated. Slot 49 allows the opposing walls 48a, 48b to flex without causing damage to the handle 30a when the ear tube 18a is coaxially positioned in the small diameter bore portion 44. Preferably, the diameter of the small diameter bore portion 44 is such that the ear tube 18a is securely held therewithin, while allowing the ear tube 18a to slide with some resistance within the small diameter bore portion along the longitudinal direction 40.

Referring back to FIG. 3, the channel 42 also includes a large diameter bore portion 50 adjacent the small diameter bore portion 44. The large diameter bore portion 50 is configured to secure the flexible tubing branch 16a into which the ear tube 18a is inserted, when the flexible tubing branch 16a is coaxially positioned within the channel 42. The large diameter bore portion 50 is configured to prevent the flexible tubing branch 16a from being removed from the channel in a direction transverse to the longitudinal direction 40.

Referring now to FIG. 5, a sectional view of the large diameter bore portion 50 is illustrated. The flexible tubing branch 16a, with the rigid ear tube 18a inserted therewithin, is shown coaxially positioned within the large diameter bore portion 50. The upper channel portion 52 of the large diameter bore portion 50 is formed by opposing lips 54a, 54b which prevent the flexible tubing branch 16a from being removed through the upper channel portion 52 of the large diameter bore portion 50. Preferably, the diameter of the large diameter bore portion 50 is such that the flexible tubing branch 16a can be slidably inserted therewithin.

The present invention is particularly advantageous because the handles 30a, 30b may be quickly and easily installed and removed from virtually any type of stethoscope without requiring disassembly of the stethoscope. To install the handle 30a on the illustrated stethoscope 10 of FIG. 1, the rigid ear tube 18a is snapped into the small diameter bore portion 44 of the channel 42, such that the handle 30a is not in contact with the flexible tubing branch 16a. The handle 30a is moved downwardly along the ear tube 18a so that the flexible tubing branch 16a slides into the large diameter bore portion 50 of the channel 42. Installation of the handle 30b is identical. The configuration of the large diameter bore portion 50 prevents the flexible tube branch 16a from becoming dislodged from the channel 42 as the handles 30a, 30b are squeezed together by a user. Various configurations for preventing the flexible tube branch 16a from becoming dislodged from the channel 42 can be utilized. The present invention is not limited to the illustrated embodiment wherein opposing lips 54a, 54b are utilized within the large diameter bore portion 50.

Referring now to FIG. 6, another embodiment of the present invention is illustrated. A flexible member 60 extends between the handles 30a, 30b to join the two handles to form a unitary device. Indicia 62 may be placed on a member 63 mounted on the flexible member 60, as illustrated.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A handle for enabling single-handed operation of a stethoscope, comprising:

an elongated base defining a longitudinal direction; and a channel formed in said base along said longitudinal direction, said channel comprising:

a small diameter bore portion configured to secure a rigid ear tube of a stethoscope coaxially positioned within said channel; and a large diameter bore portion adjacent said small diameter bore portion, said large diameter bore portion configured to secure flexible tubing connected to said ear tube, wherein said flexible tubing is coaxially positioned within said channel.

2. A handle according to claim 1 wherein said large diameter bore portion is configured to prevent said flexible tubing from being removed from said channel in a direction transverse to said longitudinal direction.

3. A handle according to claim 1 further comprising a longitudinally extending slot formed in a wall of said handle small diameter bore portion.

4. A stethoscope according to claim 1 wherein said handle comprises an arcuate end portion configured to be gripped by a hand of a user.

5. A stethoscope, comprising:

an acoustical transducer;

a pair of elongated substantially rigid ear tubes each including an upper end configured for insertion into an ear of a wearer, and a lower end configured for insertion into flexible tubing;

flexible tubing acoustically connecting each ear tube lower end to said acoustical transducer;

means for biasing said upper ends of said ear tubes toward each other, said biasing means attached to said lower end of each ear tube; and a pair of elongated handles for separating said ear tube upper ends against a force of said biasing means with one hand of a user, each elongated handle removably secured to an ear tube and to flexible tubing into which said ear tube lower end is inserted.

6. A stethoscope according to claim 5 wherein each elongated handle comprises a channel formed therein along a longitudinal direction defined by said elongated handle, and wherein said channel comprises:

a small diameter bore portion configured to secure an ear tube coaxially positioned within said channel; and a large diameter bore portion adjacent said small diameter bore portion, said large diameter bore portion configured to secure flexible tubing connected to an ear tube, wherein said flexible tubing is coaxially positioned within said channel.

7. A stethoscope according to claim 6 wherein said large diameter bore portion is configured to prevent said flexible tubing from being removed from said channel in a direction transverse to said longitudinal direction.

8. A stethoscope according to claim 6 further comprising a longitudinally extending slot formed in a wall of said handle small diameter bore portion.

9. A stethoscope according to claim 5 wherein each handle comprises an arcuate end portion configured to be gripped by a hand of a user.

10. A stethoscope according to claim 9 wherein said arcuate end portion of each handle extends in a direction away from said upper end of each rigid ear tube.

11. A stethoscope according to claim 5 further comprising a flexible member extending between said handles.

12. A stethoscope according to claim 5 wherein each handle comprises polymeric material.

13. A stethoscope, comprising:

an acoustical transducer;

a pair of elongated substantially rigid ear tubes each including an upper end configured for insertion into an ear of a wearer, and a lower end configured for insertion into flexible tubing;

flexible tubing acoustically connecting each ear tube lower end to said acoustical transducer;

means for biasing said upper ends of said ear tubes toward each other, said biasing means attached to said lower end of each ear tube; and a pair of elongated handles for separating said ear tube upper ends against a force of said biasing means with one hand of a user, each elongated handle removably secured to an ear tube and to said flexible tubing into which said ear tube lower end is inserted, wherein each elongated handle comprises:

an arcuate end portion configured to be gripped by a hand of a user; and a channel formed therein along a longitudinal direction defined by said elongated handle, said channel comprising a small diameter bore portion configured to secure an ear tube coaxially positioned within said channel, and a large diameter bore portion adjacent said small diameter bore portion, said large diameter bore portion configured to secure flexible tubing connected to an ear tube, wherein said flexible tubing is coaxially positioned within said channel.

14. A stethoscope according to claim 13 wherein said large diameter bore portion is configured to prevent said flexible tubing from being removed from said channel in a direction transverse to said longitudinal direction.

15. A stethoscope according to claim 13 further comprising a longitudinally extending slot formed in a wall of said handle small diameter bore portion.

16. A stethoscope according to claim 13 wherein said arcuate end portion of each handle extends in a direction away from said upper end of each rigid ear tube.

17. A stethoscope according to claim 13 further comprising a flexible member extending between said handles.

18. A stethoscope according to claim 13 wherein each handle comprises polymeric material.

* * * * *